United States Patent
Namba

(10) Patent No.: US 12,287,475 B2
(45) Date of Patent: Apr. 29, 2025

(54) ENDOSCOPE SYSTEM AND METHOD OF OPERATING THE SAME

(71) Applicant: FUJIFILM Corporation, Tokyo (JP)

(72) Inventor: Sora Namba, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 124 days.

(21) Appl. No.: 18/460,179

(22) Filed: Sep. 1, 2023

(65) Prior Publication Data

US 2023/0418044 A1    Dec. 28, 2023

Related U.S. Application Data

(63) Continuation of application No. PCT/JP2022/004048, filed on Feb. 2, 2022.

(30) Foreign Application Priority Data

Mar. 3, 2021    (JP) .................... 2021-033736

(51) Int. Cl.
G02B 23/24    (2006.01)

(52) U.S. Cl.
CPC ..... G02B 23/2438 (2013.01); G02B 23/2484 (2013.01)

(58) Field of Classification Search
CPC ............... G02B 23/24; G02B 23/2484; G02B 23/2438; G02B 23/2415; A61B 1/00; A61B 1/045; A61B 1/00045
USPC .................................................. 348/65, 45
See application file for complete search history.

(56) References Cited

U.S. PATENT DOCUMENTS

| | | | |
|---|---|---|---|
| 5,617,136 A | 4/1997 | Iso et al. | |
| 2009/0105544 A1 | 4/2009 | Takahira | |
| 2015/0272429 A1* | 10/2015 | Shigeta | A61B 1/0002 348/65 |
| 2016/0330365 A1 | 11/2016 | Maruyama et al. | |
| 2021/0044757 A1 | 2/2021 | Kuriyama et al. | |

FOREIGN PATENT DOCUMENTS

| | | |
|---|---|---|
| JP | H07-289507 A | 11/1995 |
| JP | 2009-100935 A | 5/2009 |
| JP | 2013-230319 A | 11/2013 |
| JP | 2016-209232 A | 12/2016 |

(Continued)

OTHER PUBLICATIONS

International Search Report issued in PCT/JP2022/004048; mailed Apr. 19, 2022.

(Continued)

*Primary Examiner* — Sherrie Hsia
(74) *Attorney, Agent, or Firm* — Studebaker Brackett PLLC

(57) ABSTRACT

A lens driving processor is configured to drive a zoom lens in accordance with pressing of a freeze button, and an image acquisition processor is configured to select a post-press evaluation frame image having a highest evaluation value, as an optimal image, from post-press evaluation frame images as examination images for which the evaluation values have been calculated among the examination images acquired in conjunction with movement of the zoom lens during a time after the pressing in a certain time before and after the pressing of the freeze button, and to display the optimal image.

10 Claims, 16 Drawing Sheets

(56) References Cited

FOREIGN PATENT DOCUMENTS

| | | |
|---|---|---|
| JP | 2020-168164 A | 10/2020 |
| WO | 2015/182519 A1 | 12/2015 |
| WO | 2019/220584 A1 | 11/2019 |

OTHER PUBLICATIONS

International Preliminary Report On Patentability (Chapter I) and Written Opinion of the International Searching Authority issued in PCT/JP2022/004048; issued Aug. 29, 2023.

* cited by examiner

FIG. 6
EXAMPLE 1 DISTANT VIEW IMAGING
(NOT IN FOCUS)
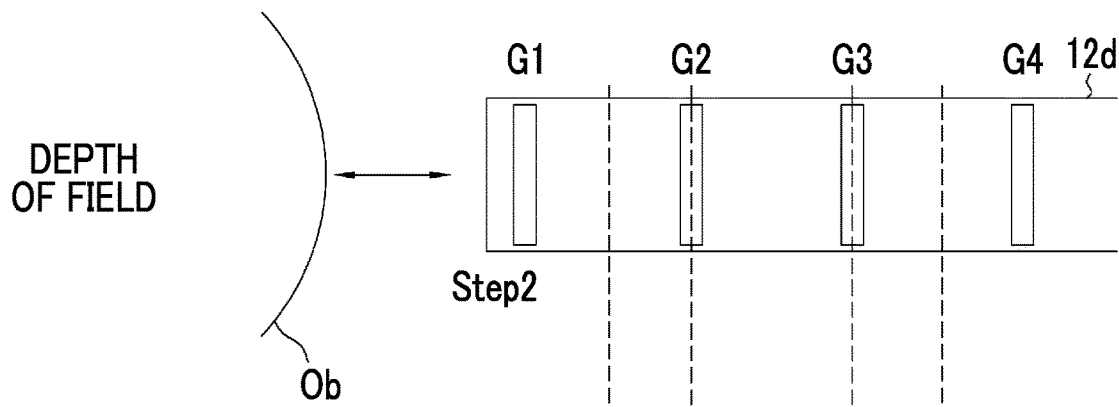
EXAMPLE 2 NEAR VIEW IMAGING
(NOT IN FOCUS)
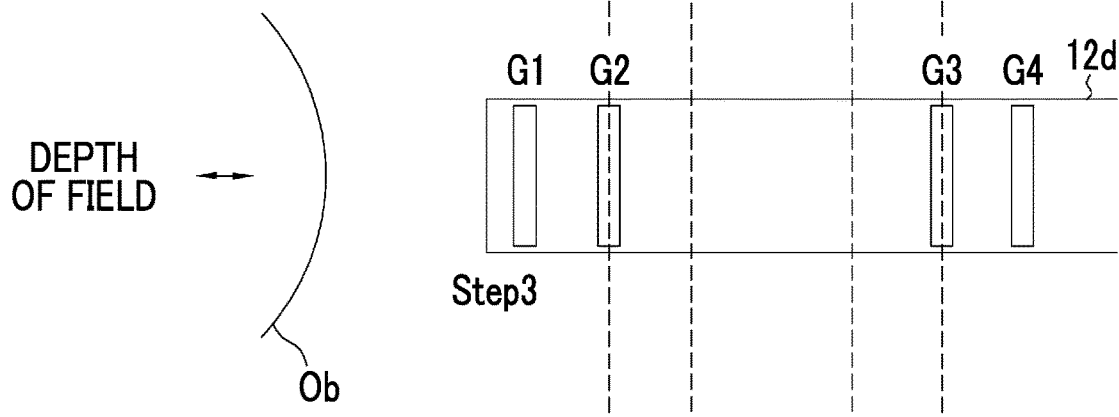
EXAMPLE 3 NEAR VIEW IMAGING
(IN FOCUS)
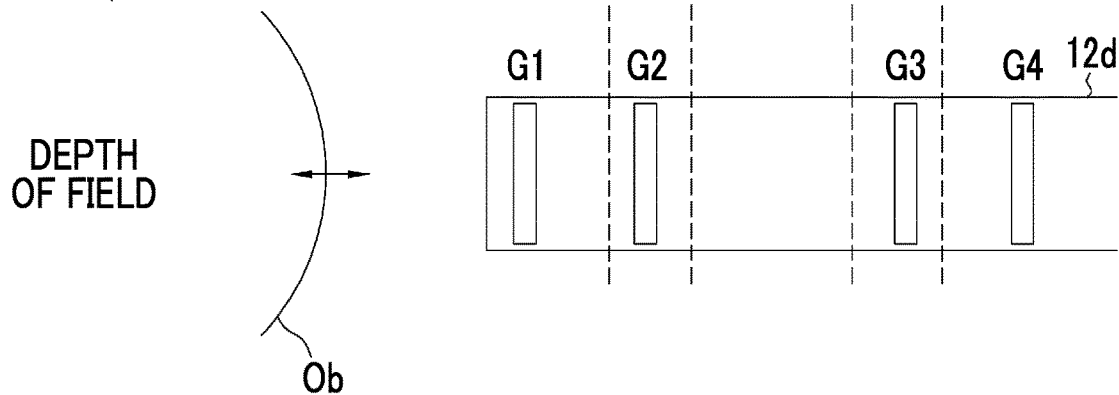

ENDOSCOPE SYSTEM AND METHOD OF OPERATING THE SAME

CROSS-REFERENCE TO RELATED APPLICATIONS

This application is a Continuation of PCT International Application No. PCT/JP2022/004048 filed on 2 Feb. 2022, which claims priority under 35 U.S.C § 119(a) to Japanese Patent Application No. 2021-033736 filed on 3 Mar. 2021. The above application is hereby expressly incorporated by reference, in its entirety, into the present application.

BACKGROUND OF THE INVENTION

1. Field of the Invention

The present invention relates to an endoscope system that displays an image on which evaluation has been performed, and a method of operating the same.

2. Description of the Related Art

It has been mainly performed to obtain a still image in a case where a lesion part or the like is found in order to perform diagnosis or post-surgery evaluation after an endoscopy. Among images captured during an examination, there may be an image in which an observation site is not in focus. One of causes of this phenomenon is that a distance between an endoscope and the observation site is too short or too long in a case where an image is captured and is out of a depth of field (out-of-focus). In this case, the focus can be adjusted by moving the endoscope back and forth. However, it is difficult for a user such as a doctor to manually perform focusing because the depth of field is shallow particularly in a case where the observation site is enlarged in close proximity.

As a technique for automatically focusing on a subject, there is an autofocus mechanism of an endoscope as disclosed in WO2019/220584A1 (corresponding to US2021/0044757A1). An intraoral camera of JP2016-209232A (corresponding to US2016/0330365A1) achieves a reduction in size and weight by obtaining an image while automatically moving a focusing lens in a case where an imaging instruction is input without using an autofocus mechanism. In addition, an endoscope disclosed in JP2020-168164A reduces a burden on a user in selecting an appropriate still image by evaluating brightness or a blur amount of a captured image and automatically selecting the appropriate still image.

SUMMARY OF THE INVENTION

Since the autofocus mechanism has a problem that an optical system for imaging is increased in size and weight, there is a demand for a technique of reducing the size of the optical system of the endoscope as much as possible without incorporating the autofocus mechanism, acquiring an image in focus while maintaining a small diameter of a distal end part, and presenting the image to the user.

An object of the present invention is to provide an endoscope system and a method of operating the same with which an image in focus is obtained while reducing a size of an optical system.

An endoscope system according to an aspect of the present invention illuminates a subject and images light from the subject. The endoscope system comprises an endoscope and a processor device. The endoscope images reflected light from a subject and includes a zoom lens and a lens driving processor for driving the zoom lens. The processor device includes an image acquisition processor. The lens driving processor drives the zoom lens in accordance with pressing of a freeze button. The image acquisition processor is configured to: acquire examination images which are time-sequentially continuous images before the freeze button is pressed; acquire the examination images in conjunction with movement of the zoom lens driven by the lens driving processor during a post-press evaluation time which is a time after the pressing of the freeze button in a total evaluation time which is a certain time before and after the pressing of the freeze button; calculate evaluation values of the examination images selected as post-press evaluation frame images from the examination images acquired within the post-press evaluation time; select the post-press evaluation frame image having a highest evaluation value among the post-press evaluation frame images for which the evaluation values have been calculated, as an optimal image; and display the optimal image.

It is preferable that the image acquisition processor is configured to: store the examination images for evaluation holding frames as evaluation holding frame images from the examination images acquired during the total evaluation time; and calculate the evaluation values of the stored evaluation holding frame images.

It is preferable that the total evaluation time is a combined time of the post-press evaluation time and a pre-press evaluation time which is a time before the pressing of the freeze button, the evaluation holding frame image consists of the post-press evaluation frame image and a pre-press evaluation frame image including the examination image acquired during the pre-press evaluation time, and the image acquisition processor is configured to calculate the evaluation values of the post-press evaluation frame image and the pre-press evaluation frame image.

It is preferable that the image acquisition processor is configured to, within a range of the evaluation holding frames, store the examination images except for some frames as the pre-press evaluation frame images in the pre-press evaluation time and store the examination images of all frames as the post-press evaluation frame images in the post-press evaluation time.

It is preferable that the image acquisition processor is configured to store the examination images acquired during the total evaluation time as the evaluation holding frame images except for some frames within a range of the evaluation holding frames.

It is preferable that the total evaluation time is at least 0.5 seconds. It is preferable that the post-press evaluation time is at least 0.3 seconds. It is preferable that the evaluation value is a contrast value. It is preferable that the number of the evaluation holding frames is at least 15 frames.

It is preferable that the image acquisition processor is configured to: select an image having a highest evaluation value from the pre-press evaluation frame images, as a pre-press optimal image; select an image having a highest evaluation value from the post-press evaluation frame images, as a post-press optimal image; and select and display an image having a higher evaluation value between the pre-press optimal image and the post-press optimal image, as the optimal image.

It is preferable that the image acquisition processor is configured to, in a case where the evaluation holding frame image of which the evaluation value is equal to or greater than a threshold value is obtained, display the evaluation holding frame image of which the evaluation value is equal to or greater than the threshold value as the optimal image.

It is preferable that the image acquisition processor is configured to drive the zoom lens in a case where a distance between the subject and a distal end of the endoscope is within a range of 2 mm or more and 6 mm or less after the pressing of the freeze button.

A method of operating an endoscope system according to the aspect of the present invention is a method of operating an endoscope system that illuminates a subject and images light from the subject, and that includes an endoscope including a zoom lens and a lens driving processor for driving the zoom lens, and a processor device including an image acquisition processor, the method comprising: via the lens driving processor, a step of driving the zoom lens in accordance with pressing of a freeze button; and, via the image acquisition processor, a step of acquiring examination images which are time-sequentially continuous images before the freeze button is pressed; a step of acquiring the examination images in conjunction with movement of the zoom lens driven by the lens driving processor during a post-press evaluation time which is a time after the pressing of the freeze button in a total evaluation time which is a certain time before and after the pressing of the freeze button; a step of calculating evaluation values of the examination images selected as post-press evaluation frame images from the examination images acquired within the post-press evaluation time; a step of selecting the post-press evaluation frame image having a highest evaluation value among the post-press evaluation frame images for which the evaluation values have been calculated, as an optimal image; and a step of displaying the optimal image.

According to the endoscope system and the method of operating the same according to the aspect of the present invention, it is possible to provide an endoscope system and a method of operating the same with which an image in focus is obtained while reducing a size of an optical system.

BRIEF DESCRIPTION OF THE DRAWINGS

FIG. 6 is an explanatory diagram showing a relationship between a distance between a position of a zoom lens and a subject, and a depth of field.

DESCRIPTION OF THE PREFERRED EMBODIMENTS

First Embodiment

Figure 1:
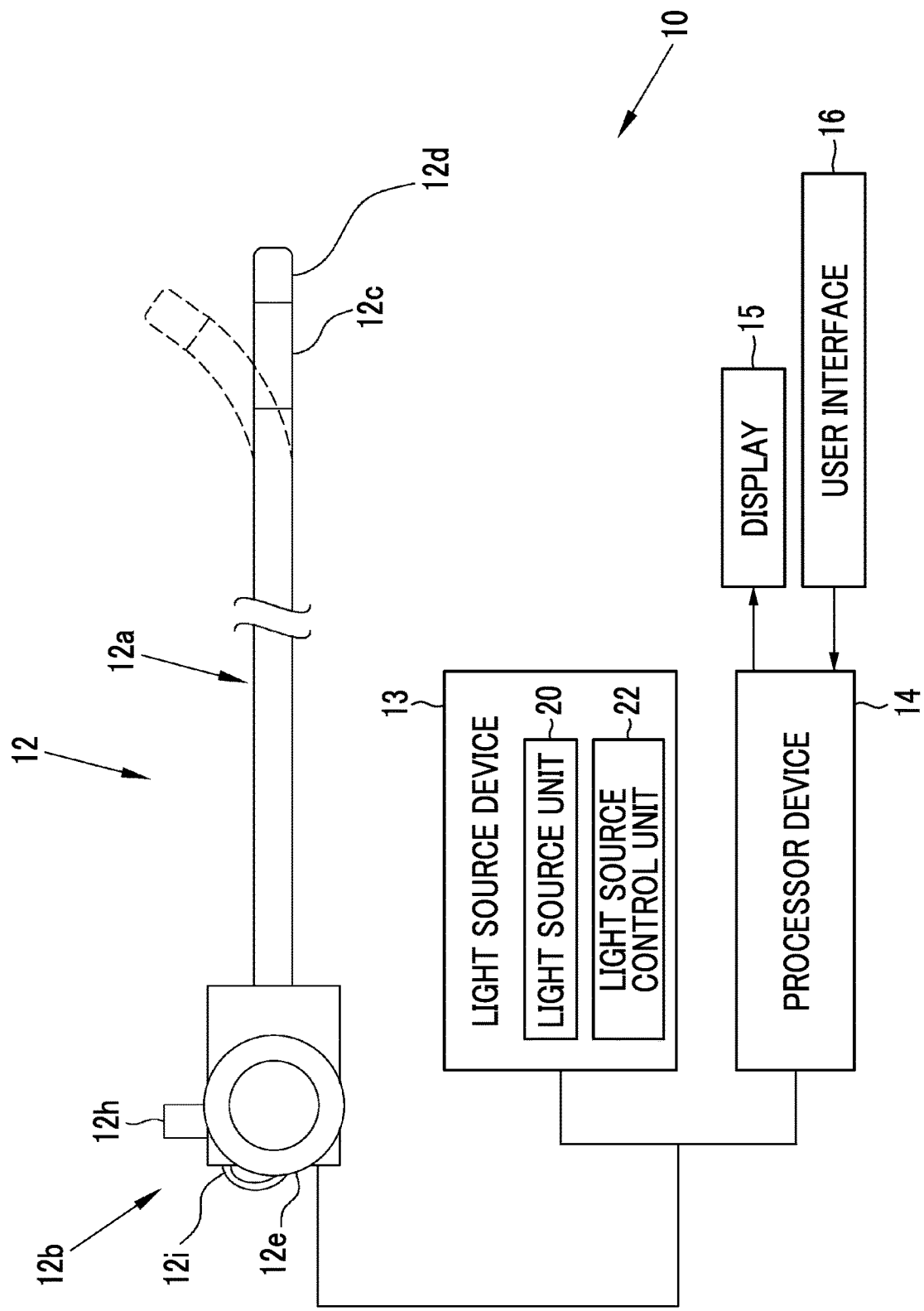
FIG. 1 is a configuration diagram of an endoscope system.

In FIG. 1, an endoscope system 10 has an endoscope 12, a light source device 13, a processor device 14, a display 15, and a user interface 16. The endoscope 12 is optically connected to the light source device 13 and is electrically connected to the processor device 14. The endoscope 12 includes an insertion part 12a to be inserted into a body of an observation target, an operating part 12b provided at a base end portion of the insertion part 12a, and a bendable part 12c and a distal end part 12d provided on a distal end side of the insertion part 12a. The bendable part 12c performs a bending operation by operating an angle knob 12e of the operating part 12b. The distal end part 12d is directed in a desired direction by the bending operation of the bendable part 12c.

In addition to the angle knob 12e, a freeze button 12h used for an acquisition instruction of a still image of a subject and a zoom operation part 12i used for an operation of a zoom lens 42 are provided on the operating part 12b.

The endoscope 12 acquires examination images that are the series of video images which are time-sequentially continuous. In the present specification, the examination images include a still image, an evaluation holding frame image, a pre-press evaluation frame image, and a post-press evaluation frame image. In a case where it is desired to acquire a still image which is an examination image of one frame while the examination image is captured, an acquisition instruction of the still image is transmitted to the endoscope 12 and the processor device 14 by pressing the freeze button 12h. A memory (not shown) for storing a still image may be connected to the processor device 14.

The processor device 14 is electrically connected to the display 15 and the user interface 16. The display 15 outputs and displays an examination image, information accompanying the examination image, and the like. The user interface 16 includes a keyboard, a mouse, a touch pad, a microphone, and the like, and has a function of receiving an input operation such as function setting.

Figure 2:
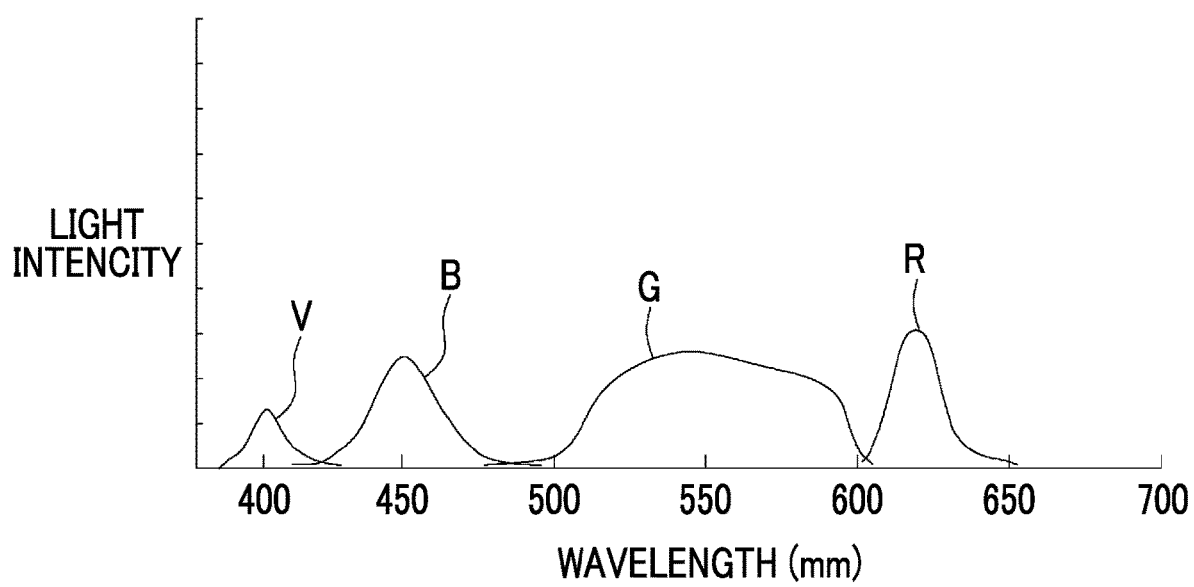
FIG. 2 is a graph showing a spectrum of white light.

A light source unit 20 of the light source device 13 emits illumination light for illuminating the subject. The light source unit 20 includes, for example, a light source such as a laser diode, a light emitting diode (LED), a xenon lamp, or a halogen lamp, and emits at least illumination light (white light) having a spectrum as shown in FIG. 2. A white color includes so-called pseudo white that is obtained by mixing violet light V, blue light B, green light G, or the red light R as shown in FIG. 2 and that is substantially equivalent to white in the imaging of the subject using the endoscope 12. Further, the light source unit 20 includes an optical filter or the like that adjusts a wavelength range, a spectrum, a light amount, or the like of the illumination light as necessary. A light source control unit 22 controls turning on or turning off of each light source constituting the light source unit 20, the amount of light emitted from each light source, and the like.

Figure 3:
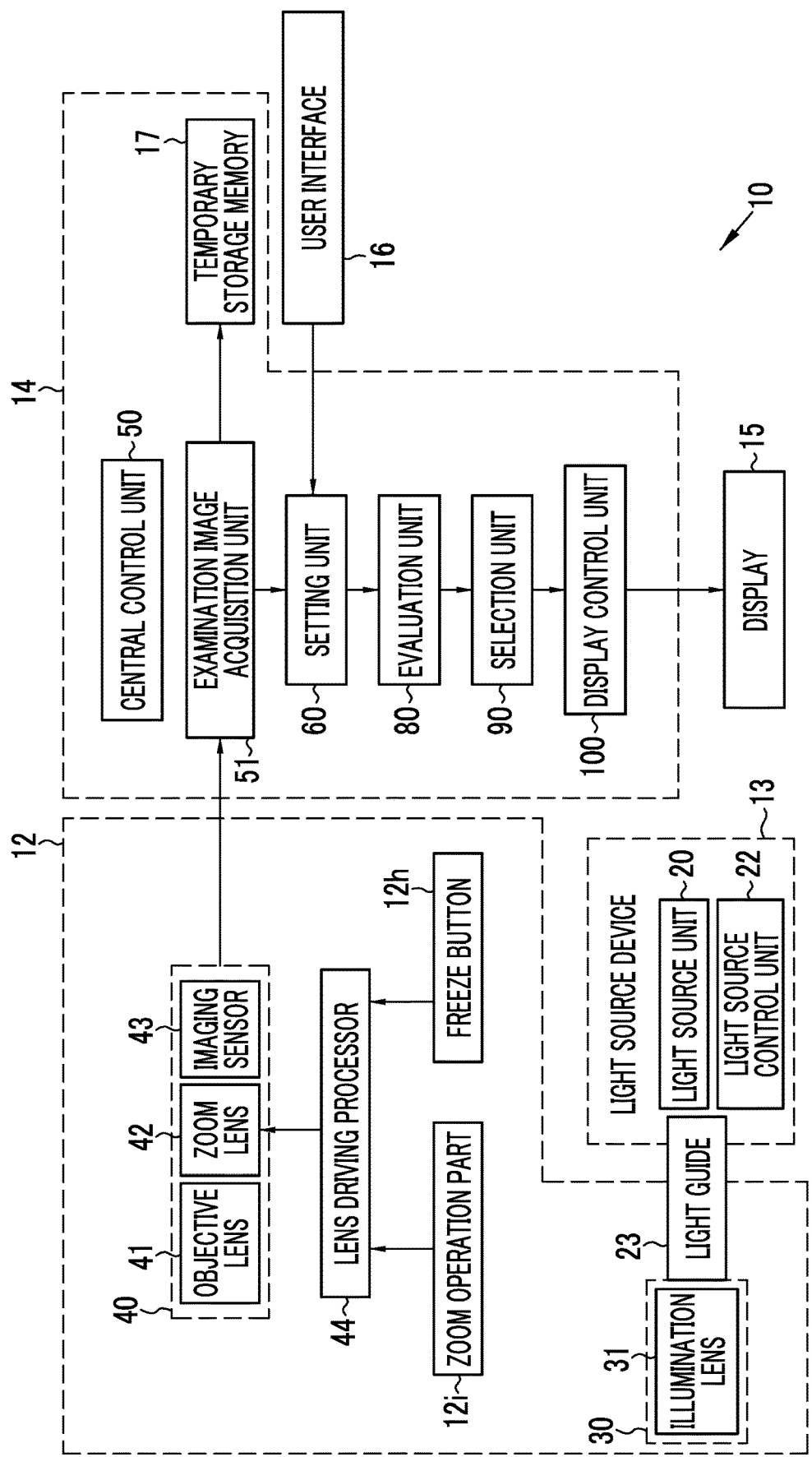
FIG. 3 is a block diagram showing a function of the endoscope system.

As shown in FIG. 3, the illumination light emitted from the light source unit 20 is incident into the endoscope 12 via a light guide 23. An illumination optical system 30 and an imaging optical system 40 are provided at the distal end part 12d of the endoscope 12. The illumination optical system 30 has an illumination lens 31, and the illumination light propagated by the light guide 23 is applied to the observation target via the illumination lens 31. The imaging optical system 40 has an objective lens 41, a zoom lens 42, and an imaging sensor 43. The light from the observation target due to the irradiation of the illumination light is incident into the imaging sensor 43 via the objective lens 41 and the zoom lens 42. Accordingly, an image of the observation target is formed on the imaging sensor 43.

Figure 4:
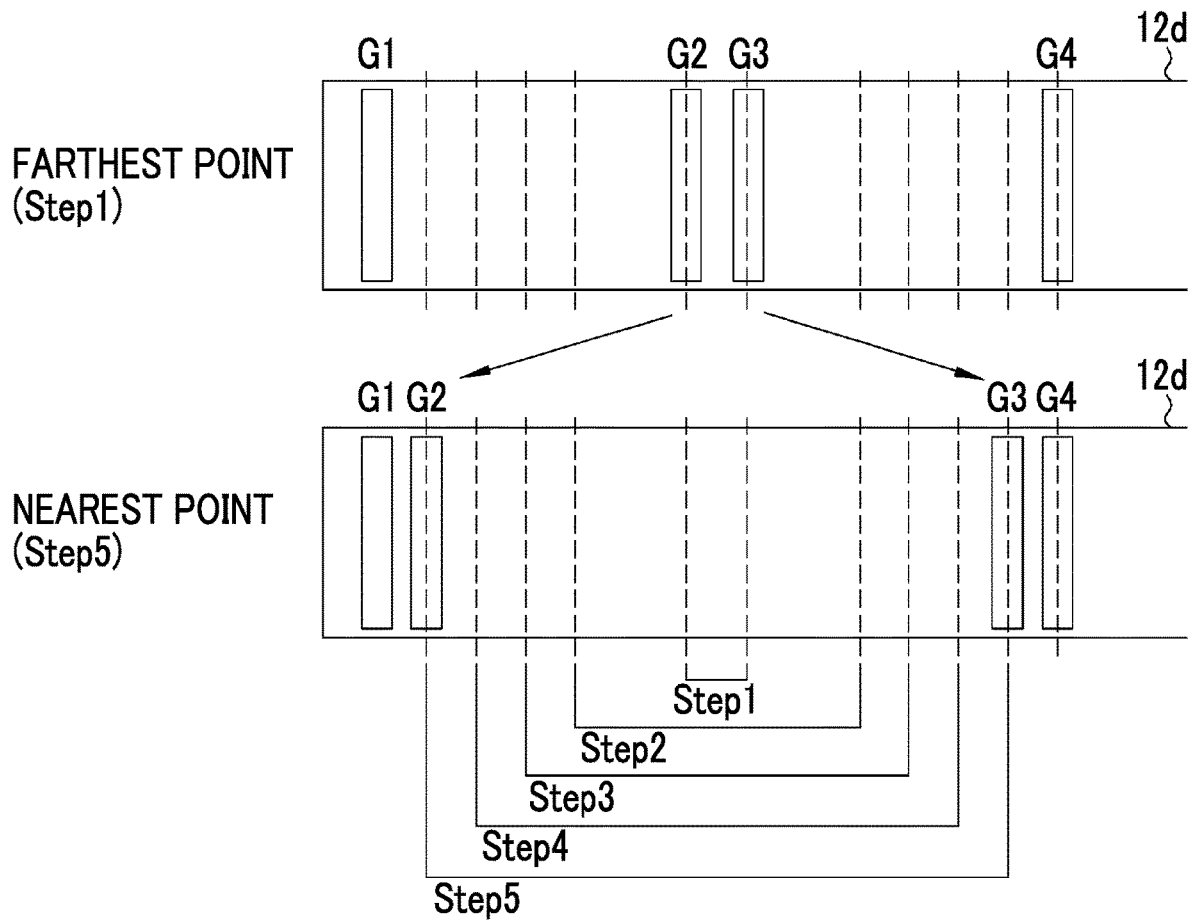
FIG. 4 is an explanatory diagram showing driving of a zoom lens.

The zoom lens 42 is a lens group for enlarging or reducing the observation target (subject). Specifically, as shown in FIG. 4, in order from the distal end side of the distal end part 12d of the endoscope 12, there are four lens groups of lenses G1, G2, G3, and G4. In a case where the subject is observed while being enlarged in close proximity, for example, in a case where a structure such as thin blood vessels is observed or a surgical treatment is performed, that is, in a case where near view imaging is performed, the zoom operation part 12i is operated, and the zoom lens groups G2 and G3 are moved in a direction in which the number of Steps is large such that a near view is in focus. On the other hand, in a case where the subject is observed in a wide range, for example, in a case where an infiltration range of a relatively large lesion part is confirmed, that is, in a case where a distant view imaging is performed, the zoom operation part 12i is operated, and the zoom lens groups G2 and G3 are moved in a direction in which the number of Steps is small such that a distant view is in focus.

A lens driving processor 44 moves the zoom lens groups G2 and G3 between a farthest point (Step1) and a nearest point (Step5) as shown in FIG. 4 in accordance with the operation of the zoom operation part 12i. In FIG. 4, dotted lines indicate approximate positions from Step1 to Step5 where the zoom lens groups G2 and G3 move. The zoom lens groups G2 and G3 move between a position of Step1 and a position of Step5 toward the distal end side of the distal end part 12d or toward a side opposite to the distal end side of the distal end part 12d. On the other hand, the zoom lens groups G1 and G4 are fixed. As the zoom lens groups G2 and G3 move, a depth of field, which is a range in which the subject appears to be in focus, changes. The way of moving the lens group is not limited thereto.

Figure 5:
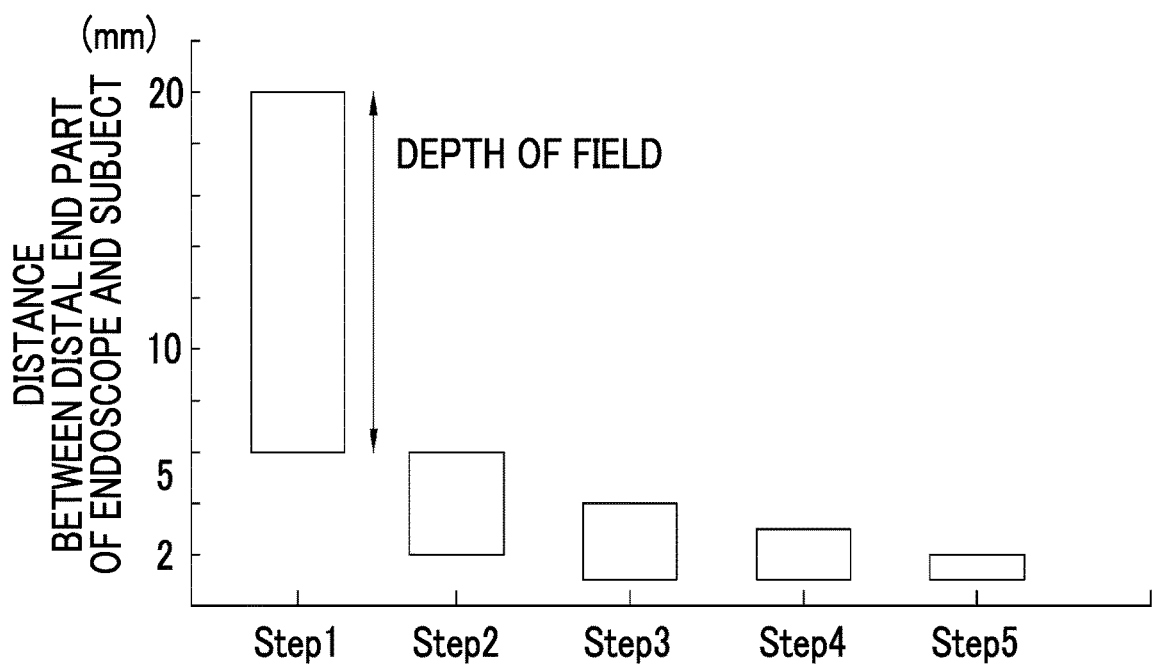
FIG. 5 is an explanatory diagram showing a depth of field.

As shown in FIG. 5, the depth of field changes depending on the positions of the zoom lens groups G2 and G3. In a case where the zoom lens groups G2 and G3 are in Step1 (refer to FIG. 4), the depth of field is deep (a position in focus is wide). On the other hand, in a case where the zoom lens groups G2 and G3 are between Step2 and Step5 (see FIG. 4), the depth of field is shallower (a position in focus is narrower) than in a case where the zoom lens groups G2 and G3 are in Step1. The shallower the depth of field, the more difficult it is to perform the focus adjustment. In particular, as shown in FIG. 6, in a case of the near view imaging in which an examination image is captured in close proximity to a subject Ob at a high magnification, in addition to the shallower depth of field, an influence of the movement of the subject side, such as a peristaltic motion, becomes large, which makes it difficult to focus on the subject.

FIG. 6 shows an example of a relationship between a distance between the positions of the zoom lens groups G2 and G3 and the subject Ob, and the depth of field. In Example 1, the zoom lens groups G2 and G3 are located in Step2, which is suitable for a case of the distant view imaging for observing a wide range, but the depth of field is in front of the subject Ob, and thus the subject is not in focus. In addition, in Example 2, the zoom lens groups G2 and G3 are located in Step3, which is suitable for a case of the near view imaging in which a smaller object is observed in an enlarged manner, but the depth of field is covered inside the back of the subject Ob, and thus the subject is not in focus. On the other hand, Example 3 is an example of performing the near view imaging as in Example 2, but since the zoom lens groups G2 and G3 are located between Step2 and Step3, and the depth of field is exactly on a front side of the subject Ob, so that the subject is in focus. In order to obtain a still image in focus, it is necessary to move the zoom lens groups G2 and G3 such that the depth of field comes to the surface of the subject Ob as in Example 3.

The lens driving processor 44 drives the zoom lens groups G2 and G3 in accordance with the pressing of the freeze button 12h, in addition to the case where the zoom operation part 12i is operated. In a case where the freeze button 12h is pressed, the zoom lens groups G2 and G3 move at a constant speed toward the distal end side of the distal end part 12d or the opposite side thereof, and an examination image is acquired in conjunction with the movement of the zoom lens groups G2 and G3 driven by the lens driving processor 44.

It is preferable to drive the zoom lens groups G2 and G3 in a case where a distance between the subject and a distal end of the endoscope 12 is within a range of 2 mm or more and 6 mm or less after the pressing of the freeze button 12h. This is because the distance between the subject and the distal end of the endoscope 12 is within the range of 2 mm or more and 6 mm or less in a case where the zoom lens groups G2 and G3 are located at positions between Step2 and Step3. Further, it is a position where the change in the depth of field is large, making it difficult to adjust the focus manually, so that it is also a range in which it is preferable to perform assistance with automatic imaging. The range in which the zoom lens groups G2 and G3 are moved is not limited to a range between Step2 and Step3 (the distance between the subject and the distal end of the endoscope 12 within the range of 2 mm or more and 6 mm or less). The movement range of the zoom lens 42 (zoom lens groups G1, G2, G3, and G4) can be optionally set.

In the case where the zoom lens groups G2 and G3 are driven, the zoom lens groups G2 and G3 may be moved from a current position toward the distal end side or in the opposite direction thereof, or the zoom lens groups G2 and G3 may be once moved to a position serving as a start point (for example, the position of Step2 or Step3) and then moved toward the distal end side or in the opposite direction thereof. With the above-described configuration, it is possible to automatically perform a zoom drive of the lens in a case of capturing a still image and to capture an image while changing the focus position. In addition, since a single actuator for a zoom adjustment mechanism is mounted without mounting the autofocus mechanism, it is possible to maintain a small diameter of the endoscope.

The imaging sensor 43 on which an image of reflected light from the subject via the objective lens 41 and the zoom lens 42 is formed is a complementary metal oxide semiconductor (CMOS) sensor, a charge-coupled device (CCD) sensor, or the like.

The imaging sensor 43 may include a monochrome imaging sensor not provided with a color filter for converting sensed light into a monochrome image signal in addition to a color imaging sensor provided with a color filter (such as a Bayer filter) for converting sensed light into a color image signal. The color imaging sensor may convert the sensed light into a CMY signal instead of an RBG signal.

In a case where a color image is acquired, the image signal includes a B image signal output from a B pixel of the imaging sensor 43, a G image signal output from a G pixel of the imaging sensor 43, and an R image signal output from an R pixel of the imaging sensor 43. The image signal detected by the imaging sensor 43 is transmitted to an examination image acquisition unit 51 of the processor device 14, and various kinds of signal processing and image processing such as noise reduction processing, color tone correction, and gradation correction are performed based on the image signal to generate an examination image which is a monochrome image or a color image.

The processor device 14 includes a central control unit 50, an examination image acquisition unit 51, a setting unit 60, an evaluation unit 80, a selection unit 90, and a display control unit 100. A temporary storage memory 17 is mounted on the processor device 14. In the processor device 14, a program in a program memory is operated by the central control unit 50 including an image acquisition processor, thereby implementing the functions of the examination image acquisition unit 51, the setting unit 60, the evaluation unit 80, the selection unit 90, and the display control unit 100.

In the setting unit 60, in a case where the freeze button 12h is pressed and a still image, which is an examination image for one frame, is acquired, a selection method and an evaluation method of an examination image that is a candidate for an optimal image which is the most focused examination image among the examination images (still images) can be set. During the examination, the examination image is transmitted from the examination image acquisition unit 51 to the setting unit 60, and the examination image is transmitted to the evaluation unit 80 according to the setting of the setting unit 60. Details of the setting unit 60 will be described below.

A user can set which examination image is to be evaluated before and after the freeze button 12h is pressed before or during the examination. Specifically, in addition to a total evaluation time, a pre-press evaluation time, and a post-press evaluation time shown in FIG. 7, an evaluation frame and a threshold value of an evaluation value are set. The evaluation frame refers to a frame for acquiring an examination image to be evaluated for which an evaluation value is calculated.

Figure 7:
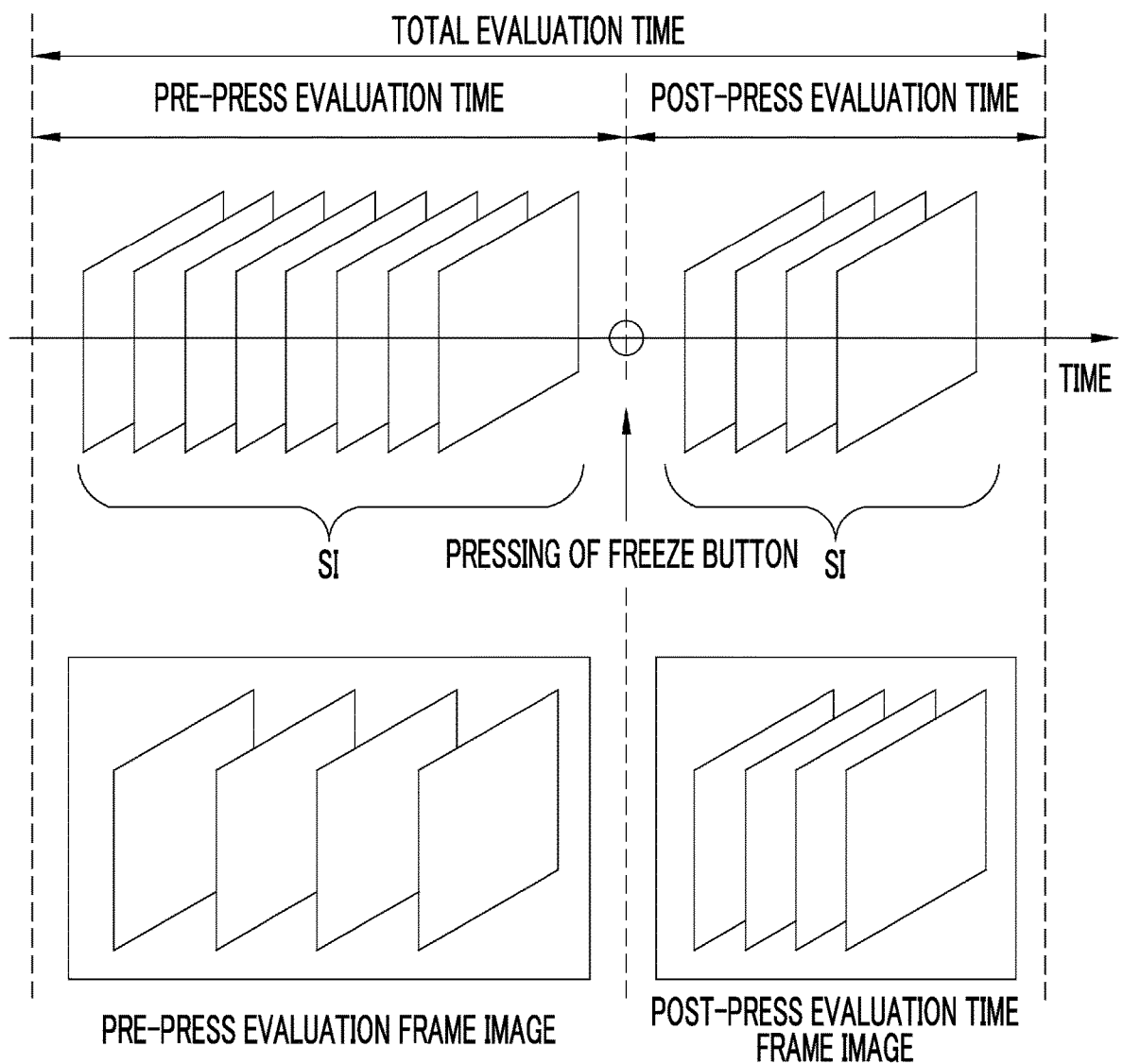
FIG. 7 is an explanatory diagram showing a total evaluation time, a pre-press evaluation time, a post-press evaluation time, a pre-press evaluation frame image, and a post-press evaluation frame image.

A method of selecting an examination image to be evaluated will be described with reference to FIG. 7. The total evaluation time is a certain time for acquiring an examination image SI to be transmitted to the evaluation unit 80 before and after the freeze button 12h is pressed. In a case where the total evaluation time is too long, the number of the examination images SI to be evaluated increases, and a pressure is put on the operation of the processor device 14 or the capacity of the temporary storage memory 17, and, in a case where the total evaluation time is too short, the number of the examination images SI to be candidates for the optimal image decreases. Therefore, the total evaluation time is preferably at least 0.5 seconds or more, and more preferably 1.0 second. The total evaluation time of 1.0 second is appropriate in a case where a frame rate of the imaging sensor 43 is 60 fps.

One frame refers to a period (a period in which one examination image is obtained) including at least a period from a timing at which the image signal is received by the imaging sensor 43 to a completion of signal reading. The total evaluation time can be optionally set on a setting screen 70 to be described below.

In the total evaluation time, a time before the freeze button 12h is pressed is the pre-press evaluation time, and a time after the freeze button 12h is pressed is the post-press evaluation time. The examination image is acquired in conjunction with the movement of the zoom lens groups G2 and G3 driven by the lens driving processor 44 during the post-press evaluation time. The post-press evaluation time is preferably a time required for the zoom lens groups G2 and G3 to move between the respective Steps. For example, in a case where a time required for moving the zoom lens groups G2 and G3 from the position of Step2 (refer to FIGS. 4 and 5) to the position of Step3 (refer to FIGS. 4 and 5) is 0.33 seconds, it is preferable that the post-press evaluation time is at least 0.3 seconds or more.

The pre-press evaluation time is a time obtained by subtracting the post-press evaluation time from the total evaluation time. For example, in a case where the total evaluation time is 1.0 second and the post-press evaluation time is 0.3 seconds, the pre-press evaluation time is 0.7 seconds. The pre-press evaluation time and the post-press evaluation time can be optionally set on the setting screen 70 to be described below. The pre-press evaluation time or the post-press evaluation time may be set to 0 seconds.

Among the examination images acquired during the pre-press evaluation time, an image of a frame selected as an evaluation target by frame setting, which will be described below, is set as a pre-press evaluation frame image. In addition, an image of a frame selected as an evaluation target by the frame setting among the examination images acquired during the post-press evaluation time is set as a post-press evaluation frame image. The pre-press evaluation frame image and the post-press evaluation frame image are stored in the temporary storage memory 17 in the processor device 14 and are transmitted to the evaluation unit 80.

Figure 8:
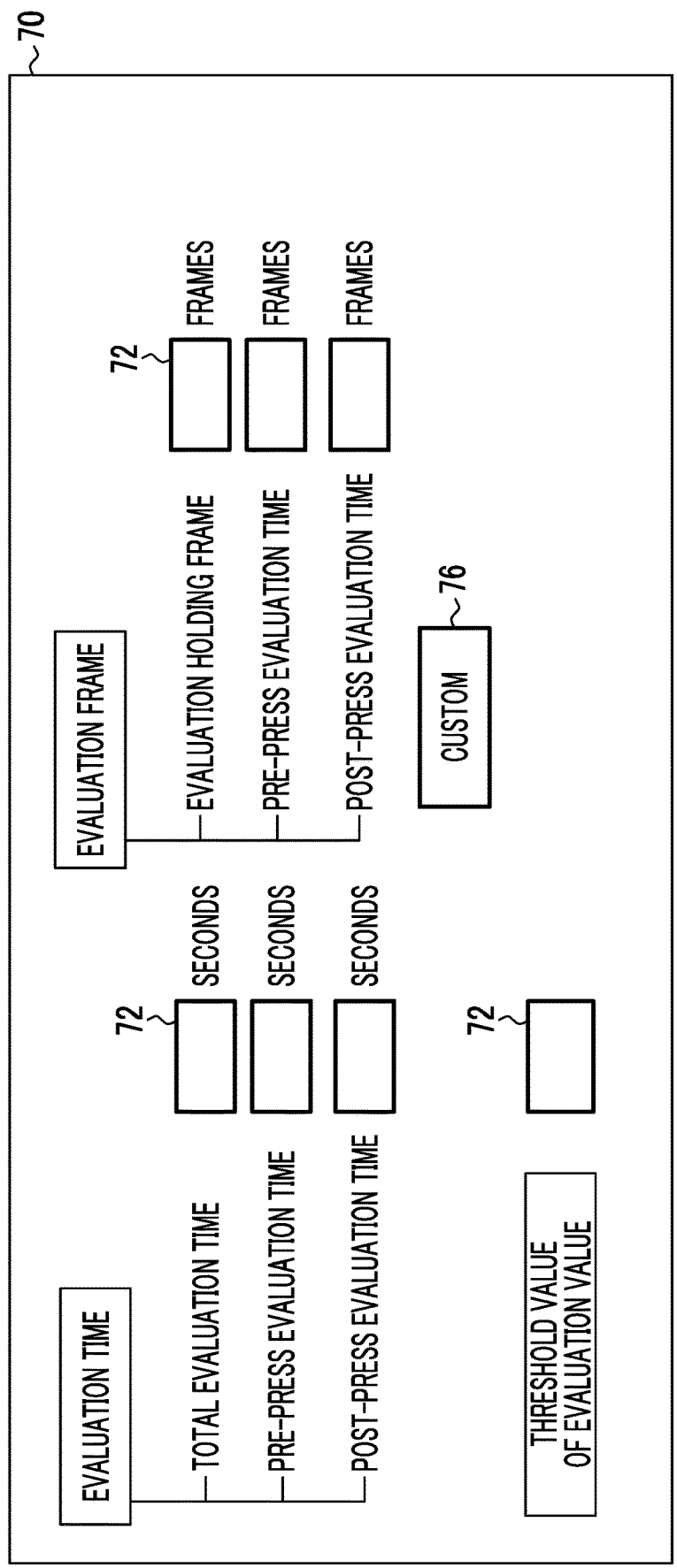
FIG. 8 is an image diagram of a setting screen.

The evaluation time including the total evaluation time, the pre-press evaluation time, and the post-press evaluation time is set from the setting screen 70 as shown in FIG. 8 via the user interface 16. The total evaluation time, the pre-press evaluation time, and the post-press evaluation time can be input from an input form 72. The input form 72 is not limited to this, and may be entered by a tab input or a voice input. With the above-described configuration, it is possible to set an examination image to be evaluated with an evaluation time such that no pressure is put on the operation of the processor or the temporary storage memory 17.

On the setting screen 70, an evaluation frame can be set in addition to the evaluation time. In the evaluation frame setting, an evaluation holding frame, which is the number of the examination images (the number of frames) to be stored in the temporary storage memory 17 within the total evaluation time, can be set. In a case where the number of the evaluation holding frames is too large, the number of the examination images to be evaluated increases, and a pressure is put on the operation of the processor device 14 or the capacity of the temporary storage memory 17, and, in a case where the number of the evaluation holding frames is too small, the number of the examination images to be candidates for the optimal image decreases. Therefore, it is preferable that the number of the evaluation holding frames is at least 15 frames or more. The evaluation holding frame can be input from the input form 72 on the setting screen 70.

The number of the evaluation frames before the freeze button 12*h* is pressed and the number of the evaluation frames after the freeze button 12*h* is pressed can also be input from the input form 72 on the setting screen 70. The number of the evaluation holding frames is obtained by adding the number of the evaluation frames before the pressing and the number of the evaluation frames after the pressing. In a case where a custom button 76 is selected, setting can be made on a custom screen 76*a* as shown in FIG. 9.

Figure 9:
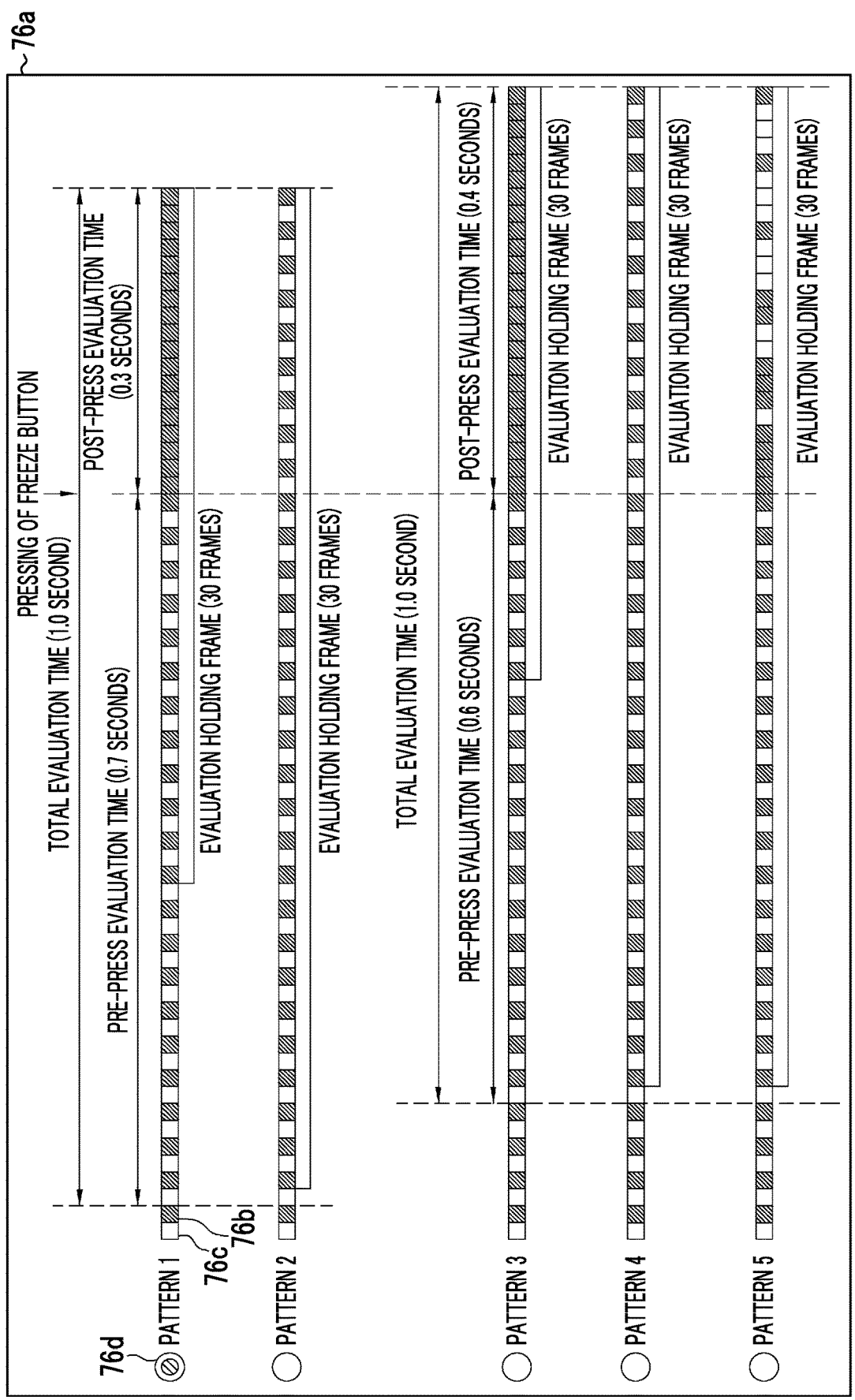
FIG. 9 is an image diagram of a custom screen.

On the custom screen 76*a* as shown in FIG. 9, an evaluation frame pattern (hereinafter, referred to as a pattern) of an examination image to be evaluated can be optionally set. The evaluation time and the evaluation frame setting input from the input form 72 on the setting screen 70 may be reflected.

In specific examples shown by Patterns 1 to 5 of FIG. 9, a shaded frame 76*b* indicates a frame to be evaluated, and an outlined frame 76*c* indicates a frame not to be evaluated. In the custom screen 76*a*, a frame can be selected with an alternate operation in which, in a case where a frame is selected via the user interface 16, the selected frame becomes an evaluation target frame, and in a case where the frame is selected again, the selection is canceled, but a selection method of a frame is not limited thereto. A template of the evaluation frame pattern as shown by Patterns 1 to 5 may be selected by a radio button 76*d*. FIG. 9 shows the custom screen 76*a* in a case where the frame rate of the endoscope 12 is 60 fps.

Pattern 1 of FIG. 9 is an example in which, in a case where the total evaluation time is 1.0 second, the post-press evaluation time is 0.3 seconds, and the number of the evaluation holding frames is 30 frames, the examination image is stored as the pre-press evaluation frame image for every other frame in the pre-press evaluation time, and the examination images of all the frames are stored as the post-press evaluation frame images in the post-press evaluation time. Pattern 1 is an evaluation frame pattern in a case where it is desired to acquire the post-press evaluation frame image preferentially over the pre-press evaluation frame image within the limited total evaluation time and evaluation holding frame.

Pattern 2 in FIG. 9 is an example in which, in a case where the total evaluation time is 1.0 second, the post-press evaluation time is 0.3 seconds, and the number of the evaluation holding frames is 30 frames, the examination image acquired during the total evaluation time is stored as the evaluation holding frame images for every other frame. The evaluation holding frame image is an examination image acquired in the evaluation holding frame. That is, Pattern 2 is an evaluation frame pattern in which the examination image is stored for every other frame in both the pre-press evaluation time and the post-press evaluation time. Pattern 2 is an evaluation frame pattern in a case where it is desired to acquire the post-press evaluation frame image and the pre-press evaluation frame image in a well-balanced manner within the limited total evaluation time and evaluation holding frame.

Pattern 3 of FIG. 9 is an example in which, in a case where the total evaluation time is 1.0 second, the post-press evaluation time is 0.4 seconds, and the number of the evaluation holding frames is 30 frames, the examination image is stored as the pre-press evaluation frame image for every other frame in the pre-press evaluation time, and the examination images of all the frames are stored as the post-press evaluation frame images in the post-press evaluation time.

Pattern 4 in FIG. 9 is an example in which, in a case where the total evaluation time is 1.0 second, the post-press evaluation time is 0.4 seconds, and the number of the evaluation holding frames is 30 frames, the examination images acquired during the total evaluation time are stored as the evaluation holding frame images at every other frame.

Pattern 5 in FIG. 9 is an example in which, in a case where the total evaluation time is 1.0 second, the post-press evaluation time is 0.4 seconds, and the number of the evaluation holding frames is 30 frames, the examination image is stored as the pre-press evaluation frame image for every other frame in the pre-press evaluation time, and, in the post-press evaluation time, four frames immediately after the freeze button 12*h* is pressed are stored as the post-press evaluation frame images and one frame is skipped, the next three frames are stored as the post-press evaluation frame images and two frames are skipped, the next two frames are stored as the post-press evaluation frame images and three frames are skipped, and then the post-press evaluation frame images are stored for every three frames.

Pattern 5 is an evaluation frame pattern in a case where it is desired to increase the number of the post-press evaluation frame images in an initial stage of the post-press evaluation time in consideration of the fact that the user presses the freeze button 12*h* at a timing in focus. The examination image may be acquired at the timing at which the freeze button 12*h* is pressed, and may be added to the pre-press evaluation frame image or the post-press evaluation frame image.

The evaluation frame pattern can be optionally created. For example, in Pattern 1, the examination image may be stored as the pre-press evaluation frame image for every two frames or three or more frames during the pre-press evaluation time. Further, the examination images acquired during the total evaluation time in Pattern 2 may be stored as the evaluation holding frame images for every two frames or three or more frames.

The examination image is stored in the temporary storage memory 17 in the processor device 14 according to the setting as described above. In a case where the freeze button 12*h* is pressed, first, the examination images for the evaluation holding frames in the pre-press evaluation time are stored in the temporary storage memory 17. Next, in a case where the examination image is acquired in conjunction with the driving of the zoom lens groups G2 and G3 in the post-press evaluation time and is stored in the temporary storage memory 17, the previous pre-press evaluation frame image is sequentially deleted in time series. In this manner, the post-press evaluation frame image is stored in the temporary storage memory 17 so as to be within the evaluation holding frame, and the examination image is stored such that no pressure is put on the temporary storage memory 17.

In a case where the evaluation holding frame is not within the total evaluation time, priority may be given to either the total evaluation time or the evaluation holding frame. It is possible to optionally set which of the total evaluation time and the evaluation holding frame is prioritized. With the above-described configuration, it is possible to set an examination image to be evaluated by a method of selecting a frame such that no pressure is put on a processor or a memory.

A threshold value of the evaluation value can be set on the setting screen 70. The evaluation value is a value obtained by evaluating a pixel value of the evaluation holding frame image, which is calculated by the evaluation unit 80. In a case where a threshold value is set for the evaluation value and in a case where the evaluation holding frame image of which the evaluation value is equal to or greater than the threshold value is obtained, the evaluation holding frame image can be set as the optimal image (refer to FIGS. 11 and 12 to be described below). The threshold value of the evaluation value can be input from the input form 72.

In accordance with the setting of the setting unit 60, the pre-press evaluation frame image and the post-press evaluation frame image are transmitted to the evaluation unit 80. The evaluation unit 80 calculates the evaluation value from the evaluation holding frame image. The evaluation holding frame image is one or more images obtained by combining the pre-press evaluation frame image and the post-press evaluation frame image, and is an examination image stored in the temporary storage memory 17 within the range of the evaluation holding frame. It is preferable that the evaluation value is a contrast value. As the evaluation value, an edge amount, a frequency, a smoothing degree, brightness, or the like may be used.

Figure 10:
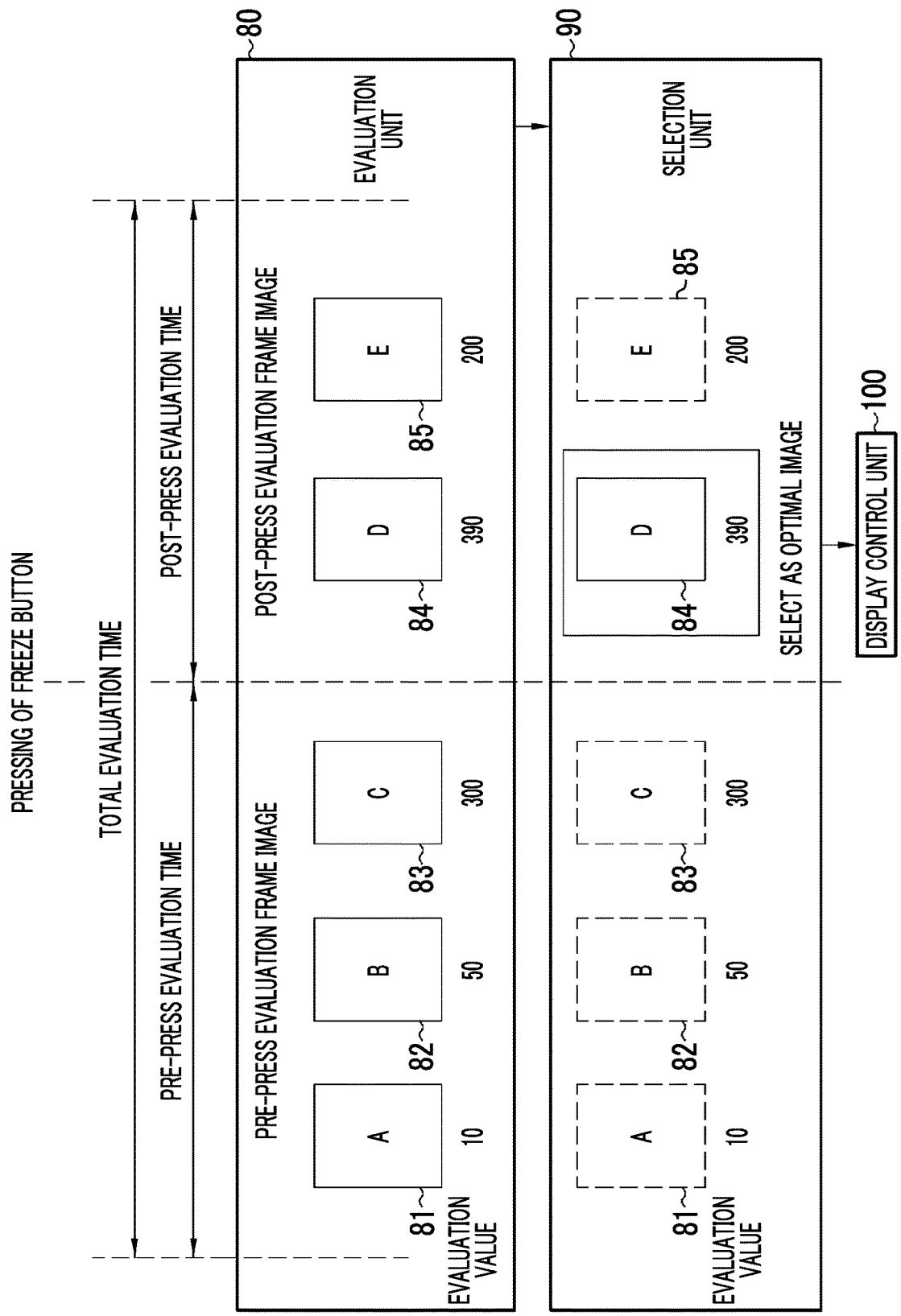
FIG. 10 is an explanatory diagram showing an evaluation unit and a selection unit in a case where a threshold value is not set.

The pre-press evaluation frame image and the post-press evaluation frame image for which the evaluation values have been calculated by the evaluation unit 80 are sequentially transmitted to the selection unit 90. As shown in FIG. 10, the selection unit 90 selects an examination image having the highest evaluation value as the optimal image among the pre-press evaluation frame image and the post-press evaluation frame image (evaluation holding frame image) for which the evaluation values have been calculated. The evaluation holding frame image selected as the optimal image is transmitted to the display control unit 100.

Specific examples of the functions of the evaluation unit and the selection unit in a case where the threshold value is not set, which are shown in FIG. 10, will be described.

Examination images A81, B82, and C83 are pre-press evaluation frame images for which the evaluation values of 10, 50, and 300 have been calculated, respectively, and examination images D84 and E85 are post-press evaluation frame images for which the evaluation values of 390 and 200 have been calculated, respectively. The examination images are acquired in the order of the examination image A81, the examination image B82, the examination image C83, the examination image D84, and the examination image E85. The examination image A81 (evaluation value 10), the examination image B82 (evaluation value 50), the examination image C83 (evaluation value 300), the examination image D84 (evaluation value 390), and the examination image E85 (evaluation value 200) are transmitted to the selection unit 90. The selection unit 90 selects the examination image D84 (evaluation value 390) having the highest evaluation value from the examination images, as the optimal image, and transmits the selected image to the display control unit 100.

Figure 11:
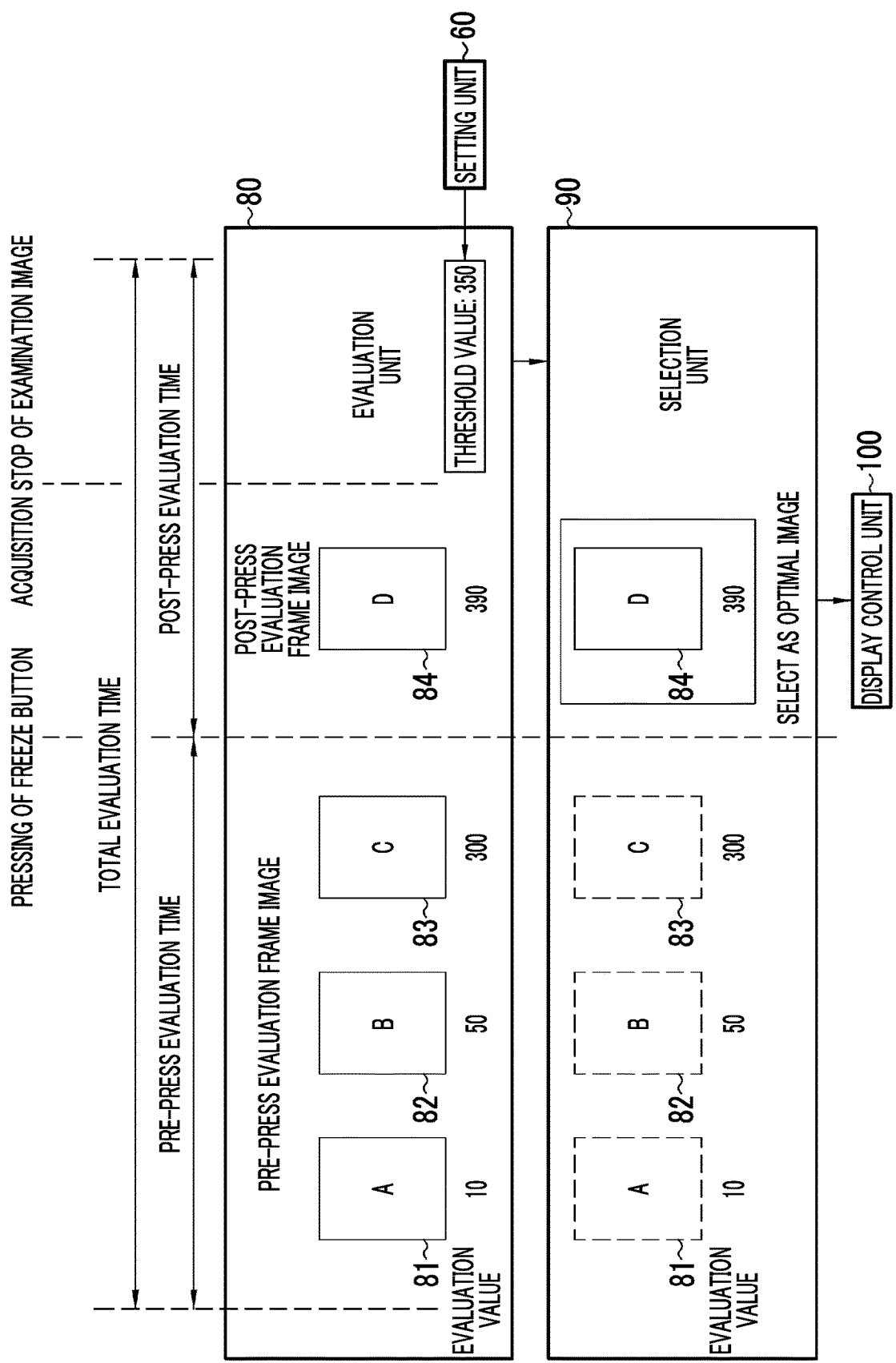
FIG. 11 is an explanatory diagram showing an evaluation unit and a selection unit in a case where a threshold value is set to 350.
Figure 12:
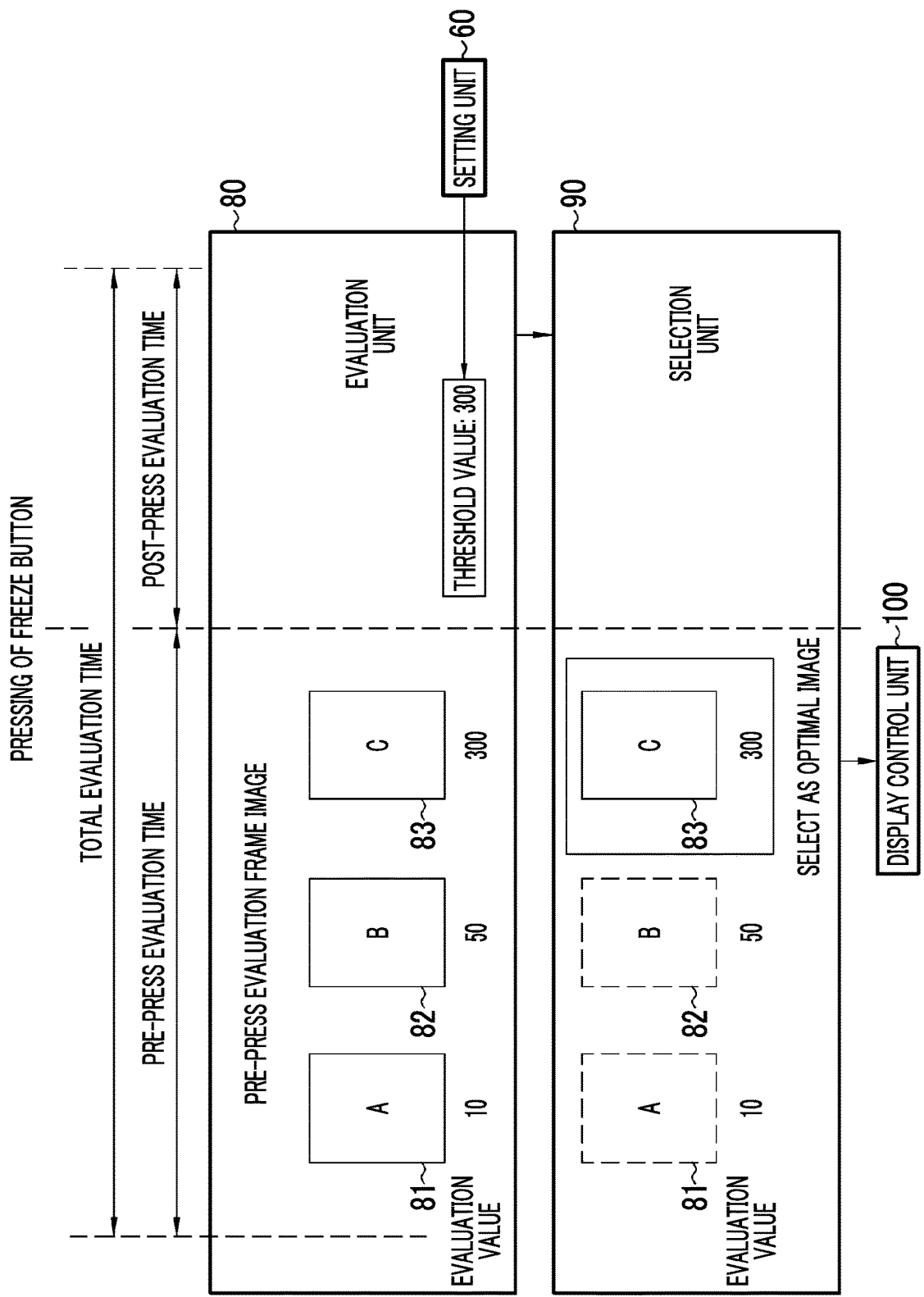
FIG. 12 is an explanatory diagram showing an evaluation unit and a selection unit in a case where a threshold value is set to 300.

In a case where the threshold value of the evaluation value is set by the setting unit 60, the optimal image is selected according to specific examples of FIGS. 11 and 12. FIG. 11 shows a specific example in which the threshold value of the evaluation value is 350. In this case, at a point in time at which the evaluation value of the examination image D84 is calculated to be 390 and transmitted to the selection unit 90, the selection unit 90 selects the examination image D84 (evaluation value 390) with the evaluation value equal to or greater than the threshold value (350), as the optimal image. Unlike the example of FIG. 10, at the point in time at which the optimal image is selected, a signal indicating the selection is transmitted to the lens driving processor 44, and the movement of the zoom lens groups G2 and G3 is stopped even in the middle of the post-press evaluation time. That is, in the specific example of FIG. 11, the examination image A81 (evaluation value 10), the examination image B82 (evaluation value 50), the examination image C83 (evaluation value 300), and the examination image D84 (evaluation value 390) are acquired, but the examination image E85 is not acquired.

FIG. 12 shows a specific example in which the threshold value of the evaluation value is 300. In this case, at the point in time at which the evaluation value of the examination image C83, which is the pre-press evaluation frame image, is calculated as 300 and transmitted to the selection unit 90, the selection unit 90 selects the examination image C83 (evaluation value 300) with the evaluation value equal to or greater than the threshold value (300), as the optimal image. In this case, at the point in time at which the optimal image is selected, a signal indicating the selection is transmitted to the lens driving processor 44, and the zoom lens groups G2 and G3 are not driven even in a case where the freeze button 12h is pressed, and the examination image C83 is displayed as the optimal image. That is, in the specific example of FIG. 12, unlike the example of FIG. 10, the examination image A81 (evaluation value 10), the examination image B82 (evaluation value 50), and the examination image C83 (evaluation value 300) are acquired, but the examination image D84 and the examination image E85 are not acquired. With the above-described configuration, by not moving the zoom lens in a case where an image in focus is acquired, it is possible to shorten a time for presenting the optimal image to the user.

Figure 13:
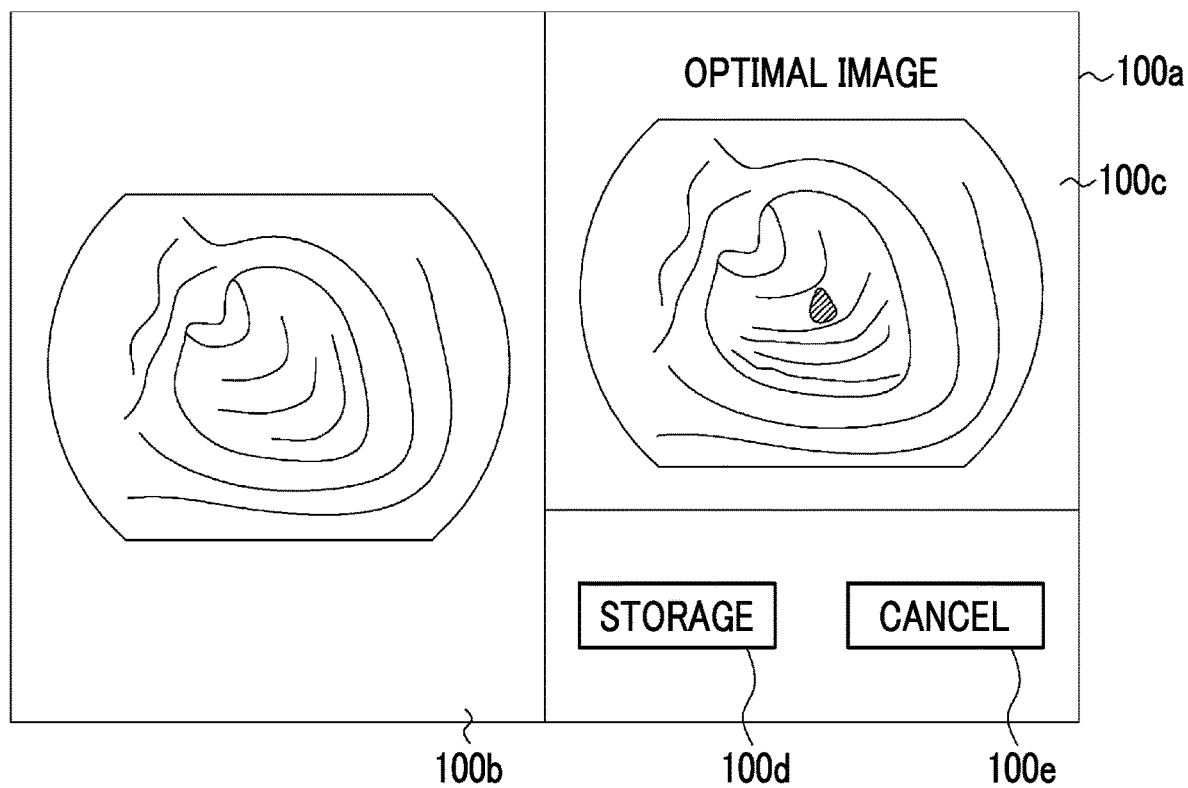
FIG. 13 is an image diagram of a display screen.

The display control unit 100 generates a display screen 100a as shown in FIG. 13 and outputs the display screen 100a to the display 15. A current examination image 100b and an optimal image 100c are displayed on the display screen 100a. In a case where a storage button 100d on the display screen 100a is selected via the user interface 16, the optimal image 100c is stored in a recording medium outside the processor device 14, such as a report memory (not shown). In a case where a cancel button 100e on the display screen 100a is selected, the display of the optimal image is canceled, and a normal display state in which only the current examination image 100b is displayed is entered. With the above-described configuration, the optimal image can be confirmed and stored during the examination.

Figure 14:
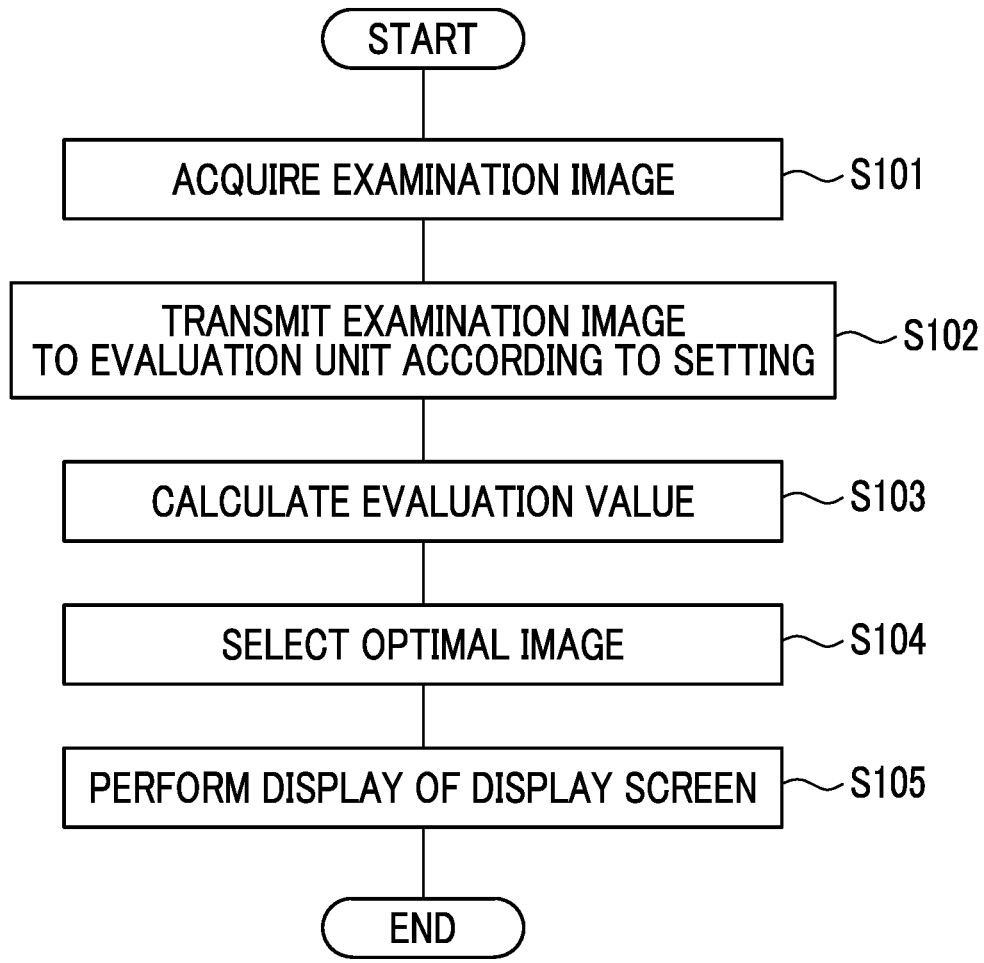
FIG. 14 is a flowchart showing a function of a first embodiment.

The series of flows from the acquisition of the examination image to the display of the display screen 100a according to the present embodiment will be described with reference to a flowchart shown in FIG. 14. First, the examination image acquisition unit 51 acquires an examination image (step S101) and transmits the examination image to the evaluation unit 80 according to the setting of the setting unit 60 (step S102). Next, an evaluation value is calculated (step S103). The selection unit 90 selects an optimal image (step S104), and the display control unit 100 generates the display screen 100a and causes the display 15 to display the display screen 100a (step S105).

Second Embodiment

Figure 15:
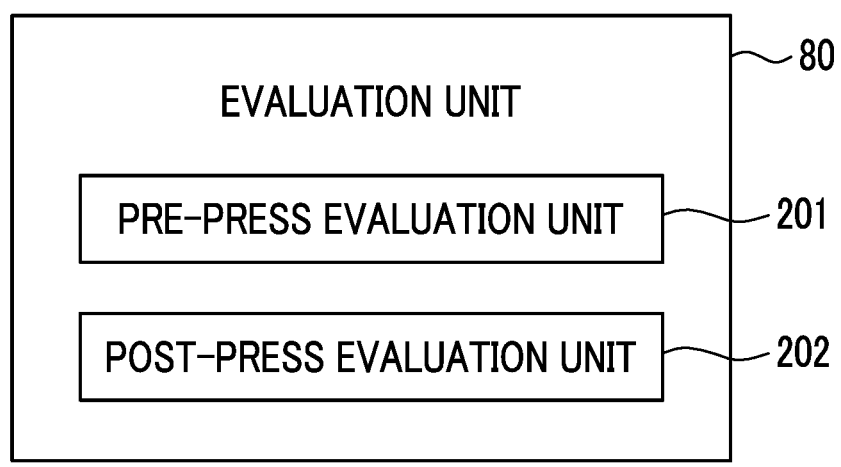
FIG. 15 is a block diagram showing a function of an evaluation unit of a second embodiment.
Figure 16:
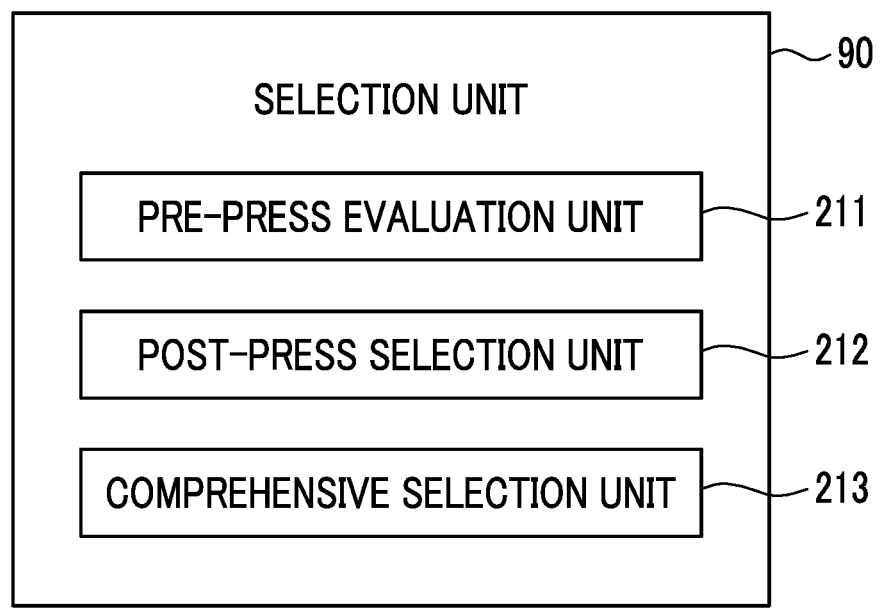
FIG. 16 is a block diagram showing a function of a selection unit of the second embodiment.

In a second embodiment, as shown in FIG. 15, the evaluation unit 80 includes a pre-press evaluation unit 201 and a post-press evaluation unit 202. Further, as shown in FIG. 16, the selection unit 90 includes a pre-press selection unit 211, a post-press selection unit 212, and a comprehensive selection unit 213. Other configurations are common to the first embodiment.

Since the present embodiment is common to the first embodiment in the processing from the acquisition of the examination image to the transmission of the examination image to the evaluation unit 80 according to the setting of the setting unit 60, and in addition, the processing after the transmission of the optimal image to the display control unit 100 by the selection unit 90, the description thereof will be omitted.

Figure 17:
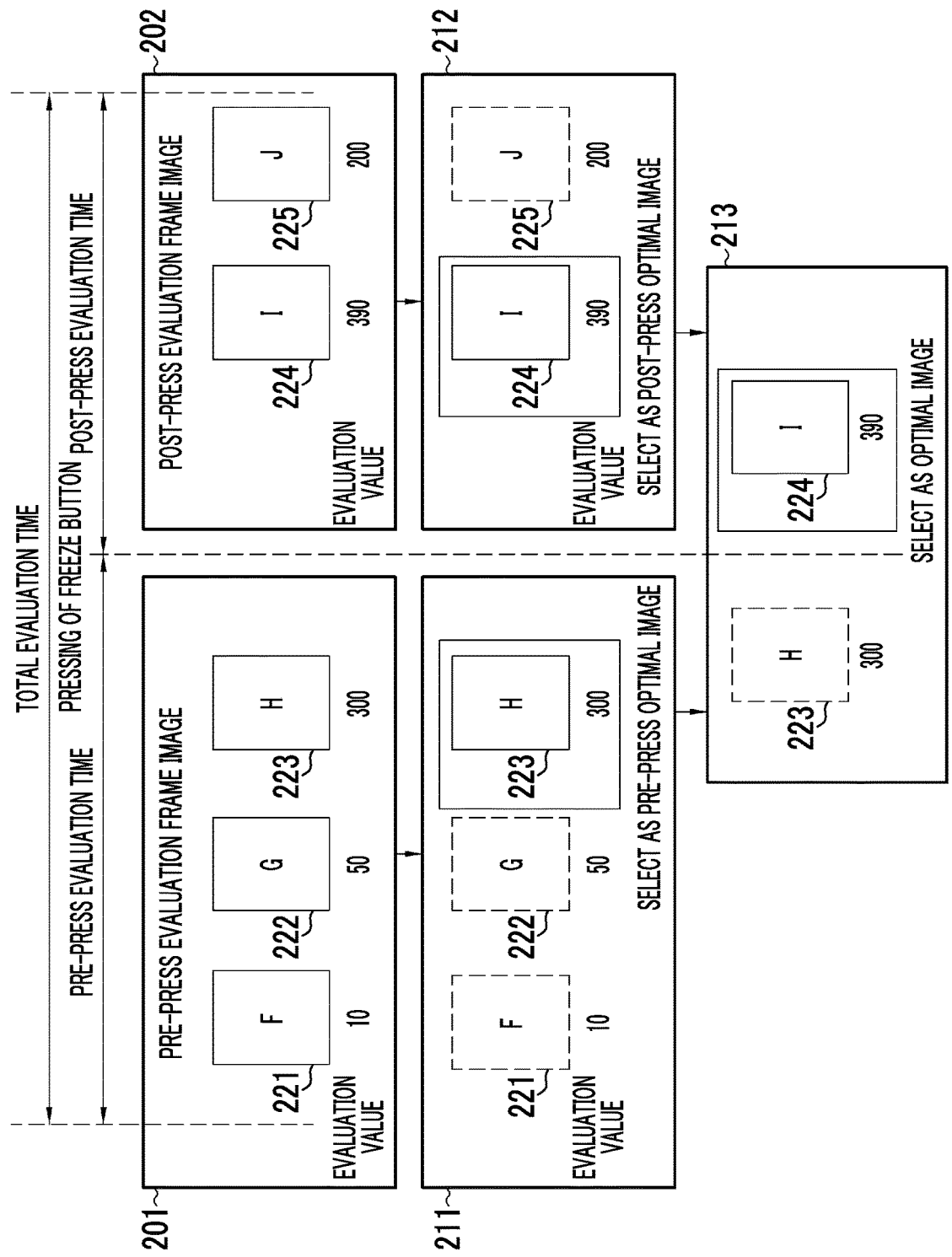
FIG. 17 is an explanatory diagram showing functions of a pre-press evaluation unit, a post-press evaluation unit, a pre-press selection unit, a post-press selection unit, and a comprehensive selection unit.

In the present embodiment, as shown in FIG. 17, in a case where the examination image is transmitted to the evaluation unit 80, the pre-press evaluation frame image is transmitted to the pre-press evaluation unit 201 and the post-press evaluation frame image is transmitted to the post-press evaluation unit 202, and the evaluation values of the pre-press evaluation frame image and the post-press evaluation frame image are calculated. The pre-press evaluation frame image for which the evaluation value has been calculated is transmitted to the pre-press selection unit 211, and the post-press evaluation frame image for which the evaluation value has been calculated is transmitted to the post-press selection unit 212.

The pre-press selection unit 211 selects an image having the highest evaluation value from the pre-press evaluation frame images, as a pre-press optimal image, and transmits the selected image to the comprehensive selection unit 213. The post-press selection unit 212 selects an image having the highest evaluation value from the post-press evaluation frame images, as a post-press optimal image, and transmits the selected image to the comprehensive selection unit 213. The comprehensive selection unit 213 selects an image having a higher evaluation value between the transmitted pre-press optimal image and post-press optimal image, as an optimal image, and transmits the selected image to the display control unit 100.

A specific example of FIG. 17 will be described. Examination images F221, G222, and H223 are pre-press evaluation frame images for which the evaluation values of 10, 50, and 300 have been calculated, respectively. The examination images are acquired in the order of the examination image F221, the examination image G222, and the examination image H223. The examination image F221 (evaluation value 10), the examination image G222 (evaluation value 50), and the examination image H223 (evaluation value 300) are transmitted to the pre-press selection unit 211. The pre-press selection unit 211 selects the examination image H223 (evaluation value 300) having the highest evaluation value from the examination image F221 (evaluation value 10), the examination image G222 (evaluation value 50), and the examination image H223 (evaluation value 300), as the pre-press optimal image, and transmits the selected image to the comprehensive selection unit 213.

An examination image 1224 and an examination image J225 are post-press evaluation frame images for which the evaluation values of 390 and 200 have been calculated, respectively. The examination images are acquired in the order of the examination image 1224 and the examination image J225. The examination image 1224 (evaluation value 390) and the examination image J225 (evaluation value 200) are transmitted to the post-press selection unit 212. The post-press selection unit 212 selects the examination image 1224 (evaluation value 390) having the highest evaluation value from the examination image 1224 (evaluation value 390) and the examination image J225 (evaluation value 200), as the post-press optimal image, and transmits the selected image to the comprehensive selection unit 213.

The comprehensive selection unit 213 compares the evaluation value of the examination image H223 (evaluation value 300), which is the pre-press optimal image, with the evaluation value of the examination image 1224 (evaluation value 390), which is the post-press optimal image. Here, since the evaluation value of the examination image H223 is 300 and the evaluation value of the examination image 1224 is 390, the comprehensive selection unit 213 selects the examination image 1224 (evaluation value 390) having a higher evaluation value as the optimal image, and transmits the selected image to the display control unit 100. Since the display screen 100a generated by the display control unit 100 is common to that of the first embodiment, the description thereof will be omitted.

The setting for selecting the optimal image from the pre-press optimal image and the post-press optimal image can be performed by the setting unit 60. In a case where the optimal image is selected by the method of the second embodiment, the threshold value is not set. With the above-described configuration, it is possible to select the optimal image from as many examination images as possible.

Figure 18:
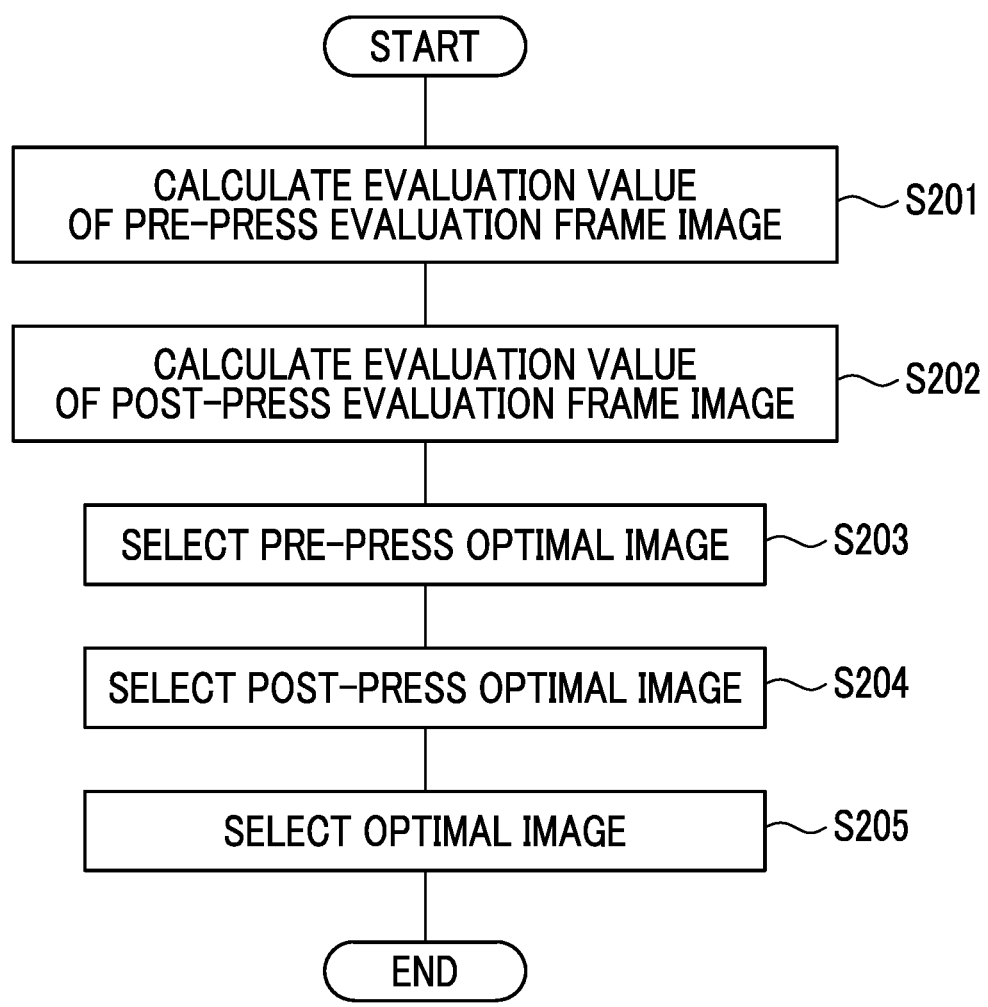
FIG. 18 is a flowchart showing a function of the second embodiment.

The series of flows from the acquisition of the examination image to the display of the display screen 100a according to the present embodiment will be described with reference to a flowchart shown in FIG. 18. The pre-press evaluation frame image is transmitted to the pre-press evaluation unit 201, and an evaluation value is calculated (step S201). The post-press evaluation frame image is transmitted to the post-press evaluation unit 202, and an evaluation value is calculated (step S202). The pre-press selection unit 211 selects an image having the highest evaluation value from the pre-press evaluation frame images, as a pre-press optimal image, and transmits the selected image to the comprehensive selection unit 213 (step S203). The post-press selection unit 212 selects an image having the highest evaluation value from the post-press evaluation frame images, as a post-press optimal image, and transmits the selected image to the comprehensive selection unit 213 (step S204). The comprehensive selection unit 213 selects an image having a higher evaluation value between the pre-press optimal image and post-press optimal image, as the optimal image, and transmits the selected image to the display control unit 100 (step S205).

In the first embodiment and the second embodiment, an example in which the processor device 14 is provided in the endoscope system 10 has been described, but the present invention is not limited thereto, and other medical devices may be used. As the endoscope 12, a rigid endoscope or a flexible endoscope may be used. In addition, a part or all of the central control unit 50, the examination image acquisition unit 51, the setting unit 60, the evaluation unit 80, the selection unit 90, and the display control unit 100 in the endoscope system 10 can be provided in, for example, a medical image processing device that communicates with the processor device 14 and cooperates with the endoscope system 10. For example, it can be provided in a diagnosis support device that acquires an image captured by the endoscope 12 directly from the endoscope system 10 or indirectly from picture archiving and communication systems (PACS). A medical service support device that is connected to various examination devices, such as a first examination device, a second examination device, . . . , and an N-th examination device, including the endoscope system 10 via a network can be provided with a part or all of the central control unit 50, the examination image acquisition unit 51, the setting unit 60, the evaluation unit 80, the selection unit 90, and the display control unit 100 in the endoscope system 10.

In the present embodiment, hardware structures of processing units that execute various kinds of processing, such as the central control unit 50, the examination image acquisition unit 51, the setting unit 60, the evaluation unit 80, the selection unit 90, and the display control unit 100, are various processors described below. The various processors include a central processing unit (CPU) that is a general-purpose processor that executes software (program) to function as various processing units, a programmable logic device (PLD) that is a processor of which a circuit configuration can be changed after manufacture, such as a field programmable gate array (FPGA), and an exclusive electric circuit that is a processor having a circuit configuration exclusively designed to execute various kinds of processing.

One processing unit may be configured of one of these various processors, or may be configured of a combination of two or more processors of the same type or different types (for example, a combination of a plurality of FPGAs or a combination of a CPU and an FPGA). In addition, a plurality of processing units may be configured of one processor. As an example in which the plurality of processing units are configured of one processor, first, as typified by a computer such as a client or a server, one processor is configured of a combination of one or more CPUs and software and this processor functions as the plurality of processing units. Second, as typified by a system on chip (SoC) or the like, a processor that realizes the functions of the entire system including the plurality of processing units by using one integrated circuit (IC) chip is used. As described above, the various processing units are configured using one or more of the various processors as a hardware structure.

Further, the hardware structure of these various processors is more specifically an electric circuit (circuitry) in a form in which circuit elements such as semiconductor elements are combined. The hardware structure of the storage unit is a storage device such as a hard disc drive (HDD) or a solid state drive (SSD).

EXPLANATION OF REFERENCES

10: endoscope system
12: endoscope
12a: insertion part
12b: operating part
12c: bendable part
12d: distal end part
12e: angle knob
12h: freeze button
121: zoom operation part
13: light source device
14: processor device
15: display
16: user interface
17: temporary storage memory
20: light source unit
22: light source control unit
23: light guide
30: illumination optical system
31: illumination lens
40: imaging optical system
41: objective lens
42: zoom lens
43: imaging sensor
44: lens driving processor
50: central control unit
51: examination image acquisition unit
60: setting unit
70: setting screen
72: input form
76: custom button
76a: custom screen
76b: shaded frame
76c: outlined frame
76d: radio button
80: evaluation unit
81: examination image A
82: examination image B
83: examination image C
84: examination image D
85: examination image E
90: selection unit
100: display control unit
100a: display screen
100b: current examination image
100c: optimal image
100d: storage button
100e: cancel button
201: pre-press evaluation unit
202: post-press evaluation unit
211: pre-press selection unit
212: post-press selection unit
213: comprehensive selection unit
221: examination image F
222: examination image G
223: examination image H
224: examination image I
225: examination image J

What is claimed is:

1. An endoscope system that illuminates a subject and images light from the subject, the endoscope system comprising:
an endoscope including a zoom lens and a lens driving processor for driving the zoom lens; and
a processor device including an image acquisition processor,
wherein the lens driving processor is configured to drive the zoom lens in accordance with pressing of a freeze button, and
the image acquisition processor is configured to:
acquire examination images which are time-sequentially continuous images before the freeze button is pressed;
acquire the examination images in conjunction with movement of the zoom lens driven by the lens driving processor during a post-press evaluation time which is a time after the pressing of the freeze button in a total evaluation time which is a certain time before and after the pressing of the freeze button;
calculate evaluation values of the examination images selected as post-press evaluation frame images from the examination images acquired within the post-press evaluation time;
select the post-press evaluation frame image having a highest evaluation value among the post-press evaluation frame images for which the evaluation values have been calculated, as an optimal image; and
display the optimal image,
wherein the image acquisition processor is further configured to:
store the examination images for evaluation holding frames as evaluation holding frame images from the examination images acquired during the total evaluation time; and
calculate the evaluation values of the stored evaluation holding frame images,
wherein the total evaluation time is a combined time of the post-press evaluation time and a pre-press evaluation time which is a time before the pressing of the freeze button, the evaluation holding frame image consists of the post-press evaluation frame image and a pre-press evaluation frame image including the examination image acquired during the pre-press evaluation time, and the image acquisition processor is further configured to calculate the evaluation values of the post-press evaluation frame image and the pre-press evaluation frame image, and wherein the image acquisition processor is further configured to, within a range of the evaluation holding frames, store the examination images except for some frames as the pre-press evaluation frame images in the pre-press evaluation time and store the examination images of all frames as the post-press evaluation frame images in the post-press evaluation time.

2. The endoscope system according to claim 1,
wherein the image acquisition processor is further configured to, within a range of the evaluation holding frames, store the examination images except for some frames acquired during the total evaluation time as the evaluation holding frame images.

3. The endoscope system according to claim 1,
wherein the total evaluation time is at least 0.5 seconds.

4. The endoscope system according to claim 1,
wherein the post-press evaluation time is at least 0.3 seconds.

5. The endoscope system according to claim 1,
wherein the evaluation value is a contrast value.

6. The endoscope system according to claim 1,
wherein the number of the evaluation holding frames is at least 15 frames.

7. The endoscope system according to claim 1,
wherein the image acquisition processor is further configured to:
select an image having a highest evaluation value from the pre-press evaluation frame images, as a pre-press optimal image;
select an image having a highest evaluation value from the post-press evaluation frame images, as a post-press optimal image; and
select and display an image having a higher evaluation value between the pre-press optimal image and the post-press optimal image, as the optimal image.

8. The endoscope system according to claim 1,
wherein the image acquisition processor is further configured to, in a case where the evaluation holding frame image of which the evaluation value is equal to or greater than a threshold value is obtained, display the evaluation holding frame image of which the evaluation value is equal to or greater than the threshold value as the optimal image.

9. The endoscope system according to claim 1,
wherein the image acquisition processor is further configured to drive the zoom lens in a case where a distance between the subject and a distal end of the endoscope is within a range of 2 mm or more and 6 mm or less after the pressing of the freeze button.

10. A method of operating an endoscope system that illuminates a subject and images light from the subject, and that includes an endoscope including a zoom lens and a lens driving processor for driving the zoom lens, and a processor device including an image acquisition processor, the method comprising:
a step of driving the zoom lens, executed by the lens driving processor, in accordance with pressing of a freeze button; and
following steps, executed by the image acquisition processor, of:
acquiring examination images which are time-sequentially continuous images before the freeze button is pressed;
acquiring the examination images in conjunction with movement of the zoom lens driven by the lens driving processor during a post-press evaluation time which is a time after the pressing of the freeze button in a total evaluation time which is a certain time before and after the pressing of the freeze button;
calculating evaluation values of the examination images selected as post-press evaluation frame images from the examination images acquired within the post-press evaluation time;
selecting the post-press evaluation frame image having a highest evaluation value among the post-press evaluation frame images for which the evaluation values have been calculated, as an optimal image; and
displaying the optimal image,
wherein the image acquisition processor further executes steps of:
storing the examination images for evaluation holding frames as evaluation holding frame images from the examination images acquired during the total evaluation time; and
calculating the evaluation values of the stored evaluation holding frame images,
wherein the total evaluation time is a combined time of the post-press evaluation time and a pre-press evaluation time which is a time before the pressing of the freeze button,
the evaluation holding frame image consists of the post-press evaluation frame image and a pre-press evaluation frame image including the examination image acquired during the pre-press evaluation time, and
the image acquisition processor further executes a step of calculating the evaluation values of the post-press evaluation frame image and the pre-press evaluation frame image, and
wherein the image acquisition processor further executes a step of, within a range of the evaluation holding frames, storing the examination images except for some frames as the pre-press evaluation frame images in the pre-press evaluation time and storing the examination images of all frames as the post-press evaluation frame images in the post-press evaluation time.

* * * * *